United States Patent
Hull (10) Patent No.: US 6,609,428 B2
(45) Date of Patent: Aug. 26, 2003

(54) NONRESONANT TECHNIQUE FOR ESTIMATION OF THE MECHANICAL PROPERTIES OF VISCOELASTIC MATERIALS

(75) Inventor: Andrew J. Hull, Newport, RI (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 123 days.

(21) Appl. No.: 09/765,487

(22) Filed: Jan. 19, 2001

(65) Prior Publication Data

US 2002/0129660 A1 Sep. 19, 2002

(51) Int. Cl.$^7$ .................................................. G01D 1/16
(52) U.S. Cl. ........................................................ 73/789
(58) Field of Search .................................... 73/787–789

(56) References Cited

U.S. PATENT DOCUMENTS 4,845,989 A * 7/1989 Titlow et al. .................. 73/597
5,614,670 A * 3/1997 Nazarian et al. ............... 73/146

* cited by examiner

*Primary Examiner*—Edward Lefkowitz
*Assistant Examiner*—C. Dickens
(74) *Attorney, Agent, or Firm*—James N. Kasischike; Michael F. Oglo; Jean-Paul A. Nasser (57) ABSTRACT

A method for estimating the real and imaginary Young's modulus, shear modulus and Poisson's ratio of a specimen at an excitation frequency. The specimen is first joined to a reciprocating test apparatus at one end with a mass positioned at the other end. The test apparatus reciprocates at the excitation frequency and accelerations are recorded at each end of the specimen. The Young's modulus is calculated from the recorded accelerations. The specimen is then joined to a reciprocating rotational test apparatus at one end with a rotational inertial mass positioned at the other end. Accelerations are recorded upon subjecting the specimen to rotational reciprocations at the excitation frequency. The shear modulus is calculated from these accelerations. Poisson's ration can be calculated from the Young's modulus and the shear modulus at the excitation frequency. All of the calculations may be performed giving both real and imaginary values.

5 Claims, 9 Drawing Sheets

NONRESONANT TECHNIQUE FOR ESTIMATION OF THE MECHANICAL PROPERTIES OF VISCOELASTIC MATERIALS

STATEMENT OF GOVERNMENT INTEREST

The invention described herein may be manufactured and used by or for the Government of the United States of America for governmental purposes without the payment of any royalties thereon or therefore.

BACKGROUND OF THE INVENTION (1) Field of the Invention

The present invention relates to a method for measuring mechanical characteristics of viscoelastic materials. More particularly, this invention provides a method for measuring complex Young's modulus, complex shear modulus, and complex Poisson's ratio of a viscoelastic material formed as a rod.

(2) Description of the Prior Art

Measuring Young's modulus and shear modulus of materials is important because these parameters significantly contribute to the static and dynamic response of a structure. Resonant techniques have been used to identify and measure these moduli for many years. These resonant methods are based on comparing the measured eigenvalues of a structure to predicted eigenvalues from a model of the same structure. The model of the structure must have well-defined (typically closed form) eigenvalues for this method to work. Additionally, resonant techniques only allow measurements at natural frequencies.

Comparison of analytical models to measured frequency response functions is another method used to estimate stiffness and loss parameters of a structure. When the analytical model agrees with one or more frequency response functions, the parameters used to calculate the analytical model are considered accurate. If the analytical model is formulated using a numerical method, a comparison of the model to the data can be difficult due to dispersion properties of the materials.

Methods also exist for measuring Young's modulus that require strain gages to be affixed to the rod. The mounting of strain gages normally requires that the gage be glued to the specimen, which locally stiffens the material. For soft viscoelastic materials, this can have an adverse impact on the estimate of the loss and stiffness. Another method for measuring stiffness and loss is by deforming the material and measuring the resistance to indentation. This method can physically damage the specimen if the deformation causes plastic deformation.

Prior art methods do not provide closed form, nonresonant techniques for measuring complex Young's modulus and complex shear modulus of a rod that contains a mass on the end when the end mass changes the dynamic response of the system. This system typically arises when an end accelerometer is attached to a rod to measure the rod's response. Frequently, the mass is large enough that it significantly changes the response of the rod.

SUMMARY OF THE INVENTION

It is a general purpose and object of the present invention to provide a method that measures the material properties of a viscoelastic material.

Yet another purpose of this invention is to provide a method for measuring the complex Young's modulus, complex shear modulus, and complex Poisson's ratio of a viscoelastic material.

Still another requirement is that the invention must provide a method for measuring the complex Young's modulus and complex shear modulus of a material at a frequency other than the resonant frequency of the system.

Accordingly, a method for estimating the real and imaginary Poisson's ratio of a specimen at an excitation frequency is provided. The specimen is first joined to a reciprocating test apparatus at one end with a mass positioned at the other end. The test apparatus reciprocates at the excitation frequency and accelerations are recorded at each end of the specimen. The Young's modulus is calculated by mathematical manipulation of the recorded accelerations. The specimen is then joined to a reciprocating rotational test apparatus at one end with an rotational inertia positioned at the other end. Accelerations are recorded upon subjecting the specimen to rotational reciprocations at the excitation frequency. The shear modulus is calculated from mathematical manipulations of these accelerations. Poisson's ratio can be calculated from the Young's modulus and the shear modulus at the excitation frequency. All of the calculations may be performed giving both real and imaginary values.

BRIEF DESCRIPTION OF THE DRAWINGS

A more complete understanding of the invention and many of the attendant advantages thereto will be readily appreciated as the same becomes better understood by reference to the following detailed description when considered in conjunction with the accompanying drawings wherein.

DESCRIPTION OF THE PREFERRED EMBODIMENT

Figure 1:
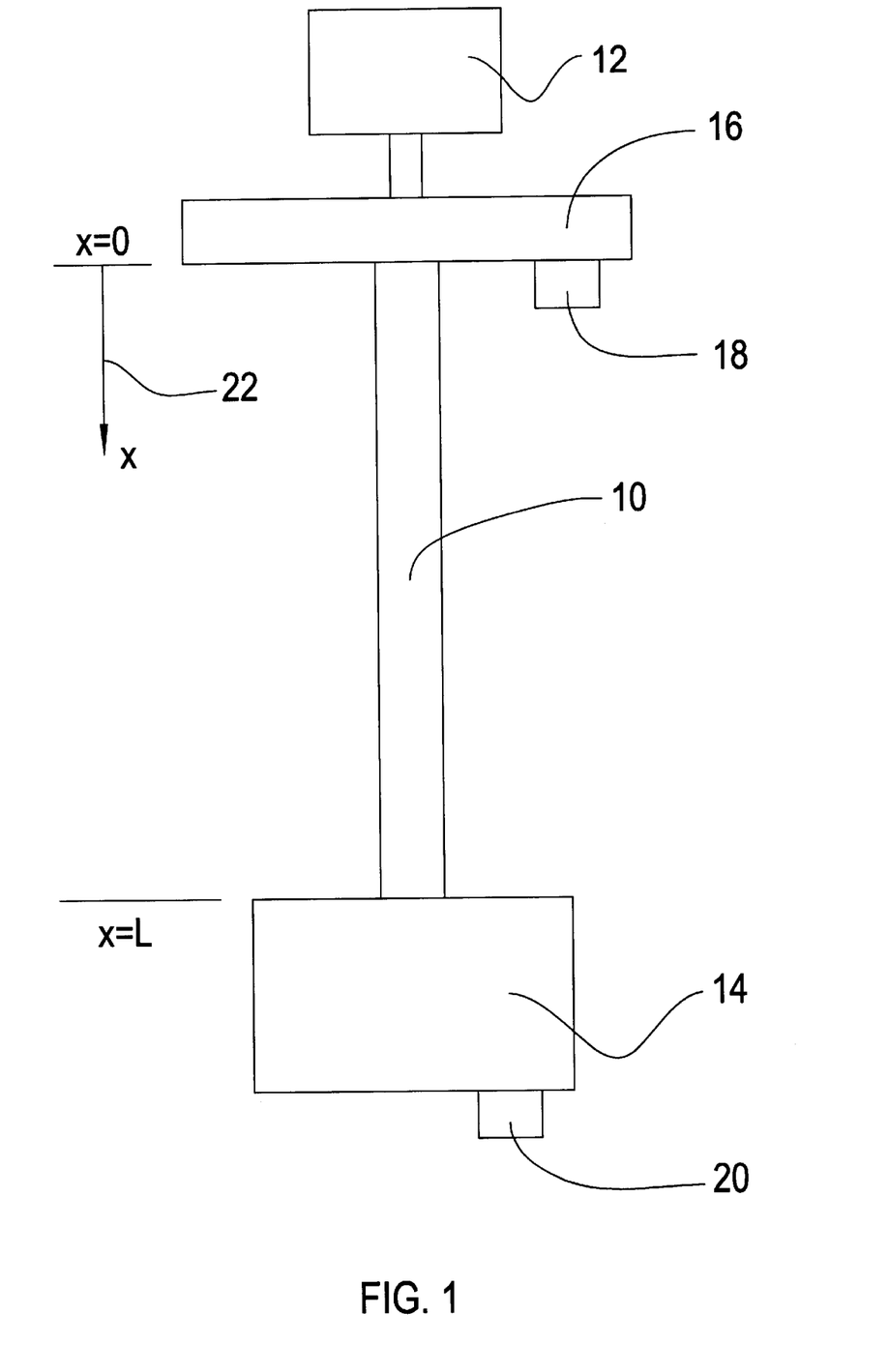
FIG. 1 shows apparatus for measurement of Young's modulus according to the current invention.

FIG. 1 shows apparatus for measurement of Young's modulus according to the current invention. One end of the test specimen rod 10 is mounted to a mechanical shaker 12 and the other end of the rod 10 is mounted to a mass 14. Shaker 12 has a shaker table 16 for mounting of instrumentation. Mass 14 is interchangeable with a second mass having a different value. An accelerometer 18 is attached to the shaker table 16 which is mechanically joined to shaker 12. A second accelerometer 20 is attached to mass 14. The measurement axis of both accelerometers 18 and 20 is in the x direction indicated by arrow 22. Shaker 12 inputs energy into rod 10 in the form of linear translation which initiates a compressional wave. The speed and loss of this wave can be measured using the two accelerometers 18 and 20, and Young's modulus can be calculated from the result. This measurement process is described below.

The system model represents rod 10 attached to shaker table 16 at x=0 and mass 14 at x=L. This mass 14 includes accelerometer 20 to measure the acceleration levels at the end of rod 10. The linear second order wave equation modeling displacement in the rod 10 is $$\frac{\partial^2 u(x,t)}{\partial t^2} - \frac{E}{\rho}\frac{\partial^2 u(x,t)}{\partial x^2} = 0, \quad (1)$$

where $u(x,t)$ is the particle displacement at location x in meters and time t in seconds, $\rho$ is the density of the rod (kg/m$^3$), and E is the frequency dependent, complex Young's modulus of elasticity (N/m$^2$) which is unknown and is to be determined using this method. The boundary at x=0 is modeled as a fixed end with harmonic motion and is expressed as $$u(0,t) = U_0 \exp(i\omega t), \quad (2)$$

where $\omega$ is the frequency of excitation (rad/s), $U_0$ is the amplitude (m), and i is the square root of $-1$. The boundary at x=L is formulated by matching the force at the end of the rod 10 to the force caused by mass 14 and is expressed as $$AE\frac{\partial u(L,t)}{\partial x} = -m\frac{\partial^2 u(L,t)}{\partial t^2}, \quad (3)$$

where A is the cross-sectional area (m$^2$) of the rod 10 and m is the mass (kg) of mass 14 at the end of the rod 10.

Equation (1) can be rewritten in the spatial domain as $$\frac{d^2 U(x,\omega)}{dx^2} + k_E^2 U(x,\omega) = 0, \quad (4)$$

where $U(x,\omega)$ is the temporal Fourier transform of the axial displacement and $k_E$ is the complex compressional wavenumber (rad/m) and is equal to $$k_E = \omega/\sqrt{E/\rho}. \quad (5)$$

Similarly, equation (2) becomes $$U(0,\omega) = U_0, \quad (6)$$

and equation (3) becomes $$AE\frac{dU(L,\omega)}{dx} = m\omega^2 U(L,\omega). \quad (7)$$

The solution to equation (4) is $$U(x,\omega) = R(\omega)\cos(k_E x) + S(\omega)\sin(k_E x), \quad (8)$$

where R and S are wave propagation constants. Applying boundary conditions (6) and (7) to equation (8), and writing the solution as a transfer function in the form of a ratio between the displacement at both ends, produces $$\frac{U(L,\omega)}{U_0} = \left[\frac{1}{\cos(k_E L) - \mu(k_E L)\sin(k_E L)}\right], \quad (9)$$

where $\mu$ is the ratio of the mass of the mass 14 to the rod 10 mass and is equal to $$\mu = \frac{m}{M}, \quad (10)$$

where M is the mass of the rod (kg) expressed as $$M = \rho A L. \quad (11)$$

The transfer function in equation (9) represents data and is a function of unknown wavenumber $k_E$. The inversion of two of these transfer functions using different attached masses will allow the experimental data to be combined and yield a closed form solution of $k_E$ and then E as a function of $\omega$. The theoretical form of these transfer functions is $$\frac{U(L,\omega)}{U_0} = T_1(\omega) = \left[\frac{1}{\cos(k_E L) - \mu_1(k_E L)\sin(k_E L)}\right], \quad (12)$$

and $$\frac{U(L,\omega)}{U_0} = T_2(\omega) = \left[\frac{1}{\cos(k_E L) - \mu_2(k_E L)\sin(k_E L)}\right], \quad (13)$$

where the subscript 1 denotes the first attached mass and the subscript 2 denotes the second attached mass. Writing equations (12) and (13) as a function of $(k_E L)\sin(k_E L)$ and then equating them yields $$\cos(k_E L) = \frac{T_2\mu_2 - T_1\mu_1}{T_1 T_2(\mu_2 - \mu_1)} = \phi, \quad (14)$$

where $\phi$ is a complex quantity. The inversion of equation (14) allows the complex wavenumber to be solved as a function of $\phi$. This solution to the real part of $k_E$ is $$\text{Re}(k_E) = \begin{cases} \frac{1}{2L}\text{Arccos}(s) + \frac{n\pi}{2L}, & n \text{ even} \\ \frac{1}{2L}\text{Arccos}(-s) + \frac{n\pi}{2L}, & n \text{ odd} \end{cases}, \quad (15)$$

where $$s = [\text{Re}(\phi)]^2 + [\text{Im}(\phi)]^2 - \sqrt{\{[\text{Re}(\phi)]^2 + [\text{Im}(\phi)]^2\}^2 - \{2[\text{Re}(\phi)]^2 + 2[\text{Im}(\phi)]^2\}}, \quad (16)$$

n is a non-negative integer and the capital A denotes the principal value of the inverse cosine function. The value of n is determined from the function s, which is a cosine function with respect to frequency. At zero frequency, n is 0. Every time s cycles through $\pi$ radians (180 degrees), n is increased by 1. When the solution to the real part of $k_E$ is found, the solution to the imaginary part of $k_E$ is then written as $$\text{Im}(k_E) = \frac{1}{L}\log_e\left\{\frac{\text{Re}(\phi)}{\cos[\text{Re}(k_E)L]} - \frac{\text{Im}(\phi)}{\sin[\text{Re}(k_E)L]}\right\}. \quad (17)$$

Once the real and imaginary parts of wavenumber $k_E$ are known, the complex valued modulus of elasticity can be determined at each frequency with $$E(\omega) = \text{Re}[E(\omega)] + i\text{Im}[E(\omega)] = \frac{\rho\omega^2}{[\text{Re}(k_E) + i\text{Im}(k_E)]^2}. \quad (18)$$

Equations (12)–(18) produce an estimate Young's modulus at every frequency in which a measurement is conducted.

Figure 2:
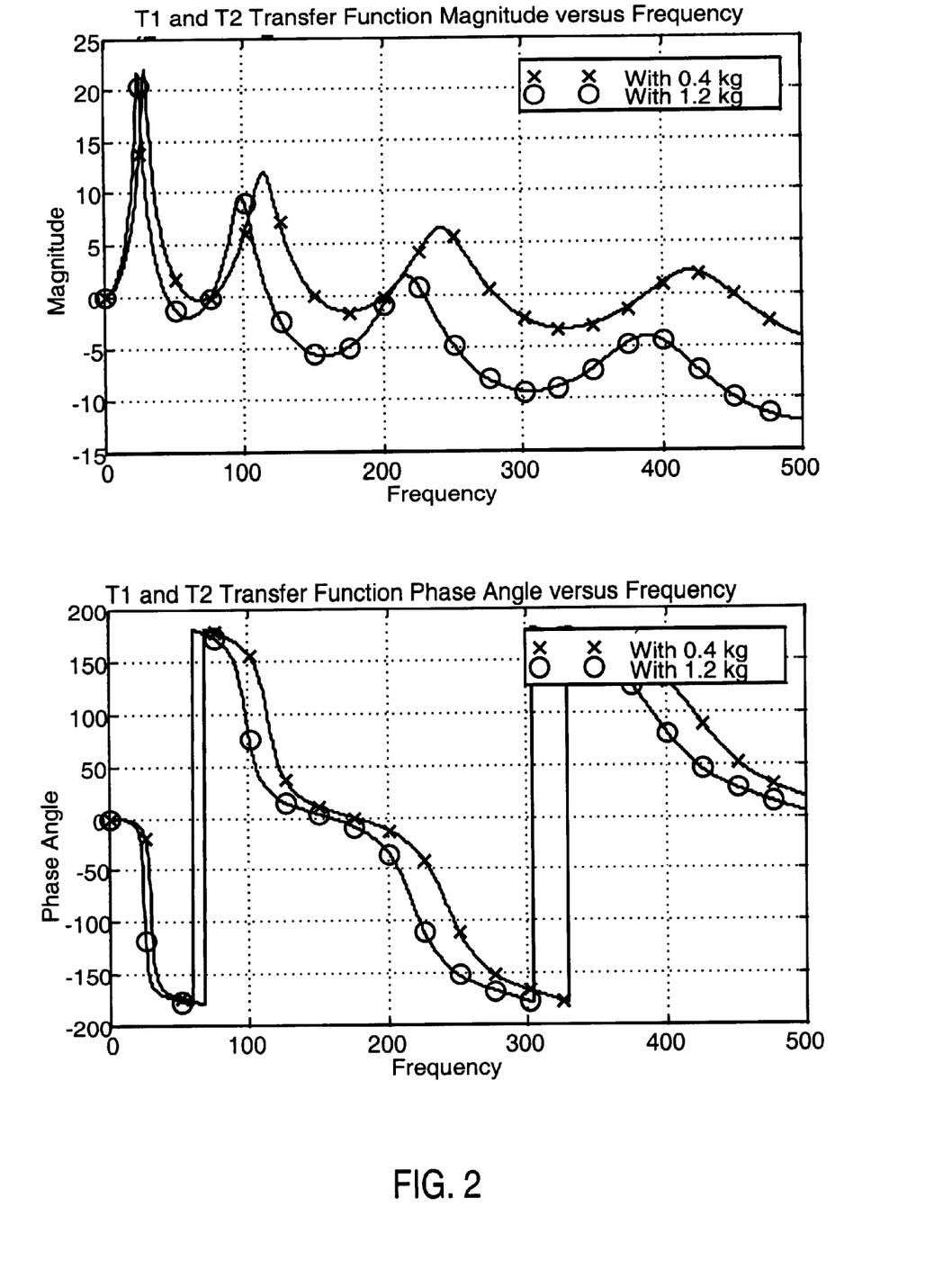
FIG. 2 is a plot of the transfer functions $T_1(\omega)$ and $T_2(\omega)$ versus frequency.
Figure 3:
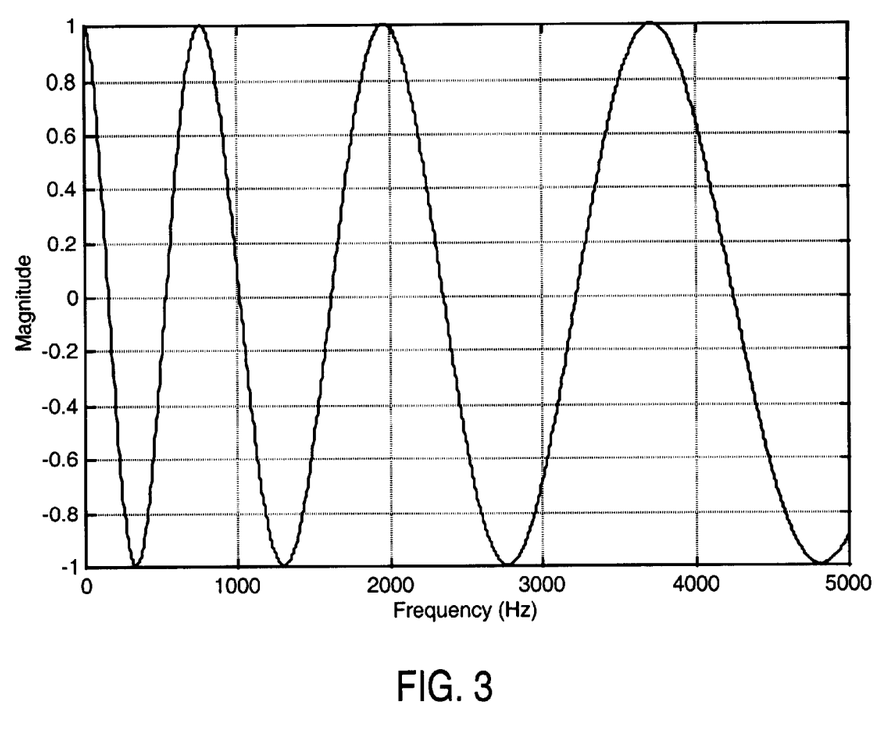
FIG. 3 is a plot of the function s versus frequency.

Numerical simulations have been conducted to determine the effectiveness of this method. A baseline problem is defined with M=4.0 kg, $m_1$=0.4 kg, $m_2$=1.2 kg, L=0.254 m, $\rho$=1200 kg/m$^3$, Re(E)=10$^8$+10$^5$ f N/m$^2$, and Im(E)=10$^7$+10$^4$ f N/m$^2$ where f is frequency in Hertz. Using these values, the mass ratios $\mu_1$ and $\mu_2$ are computed to be 0.1 and 0.3, respectively. FIG. 2 is a plot of the transfer functions $T_1(\omega)$ and $T_2(\omega)$ versus frequency and corresponds to equations (12) and (13). The top plot is the magnitude and the bottom plot is the phase angle. The first transfer function was computed using an attached mass of 0.4 kg and is depicted with x's and the second transfer function was computed using an attached mass of 1.2 kg and is shown with o's. FIG. 3 is a plot of the function s versus frequency and corresponds to equation (16). Note that although this function is a cosine with respect to frequency, the period is increasing as frequency increases. Once the values of n are known, the modulus values of E can be determined using equations (15)–(18).

Figure 4:
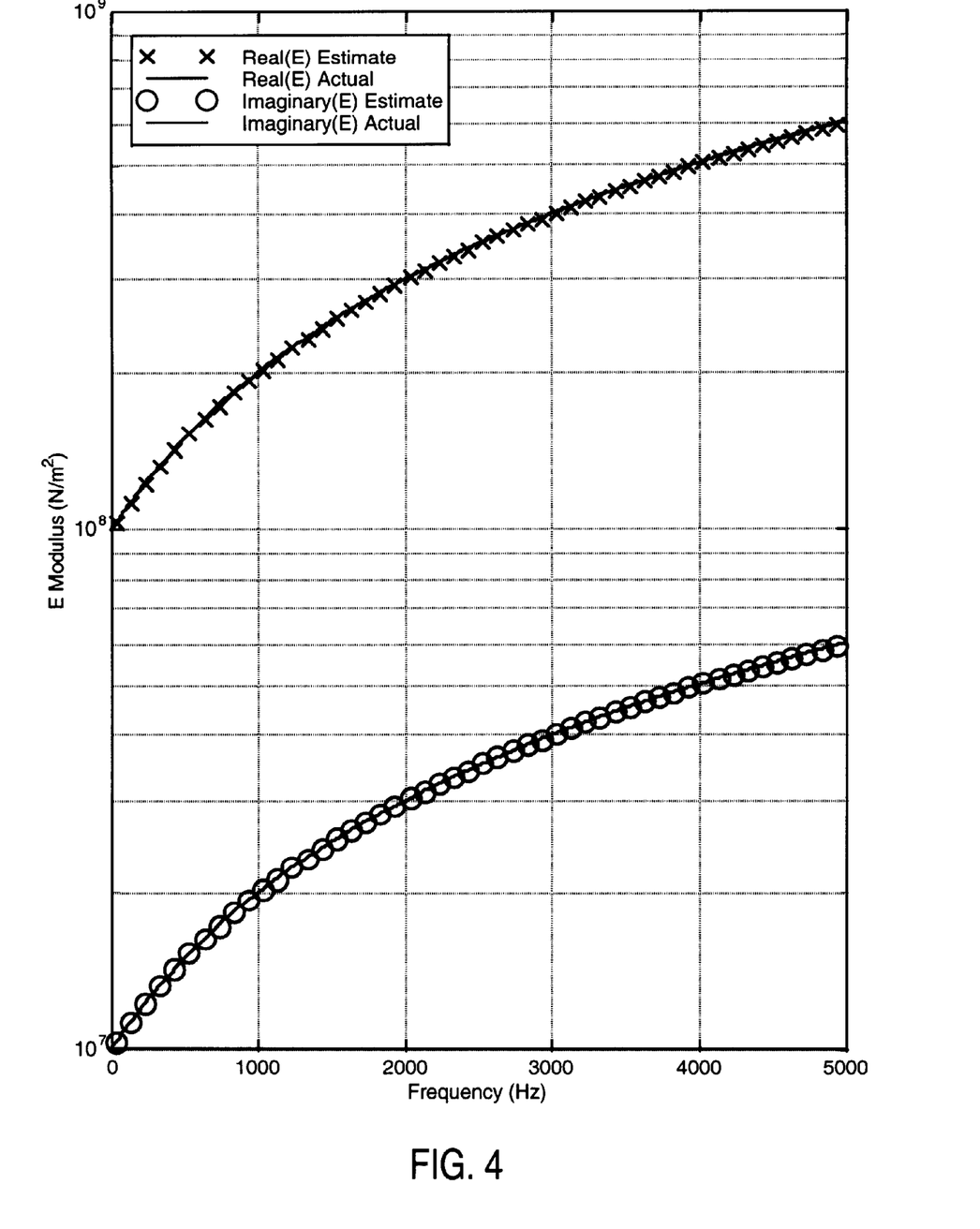
FIG. 4 is a plot of real and imaginary Young's modulus values versus frequency.

FIG. 4 is a plot of real and imaginary Young's modulus values versus frequency. The real (actual) values used to make the transfer functions are displayed as a solid line and the real (estimated) values are displayed as x's. The imaginary (estimated) values are displayed as o's. The estimated values agree at all frequency values with the actual values. This is expected because there is no noise in the date and all the parameters used to make the transfer functions are used to calculate the modulus values. No error is introduced when calculating the modulus from the transfer functions.

Figure 5:
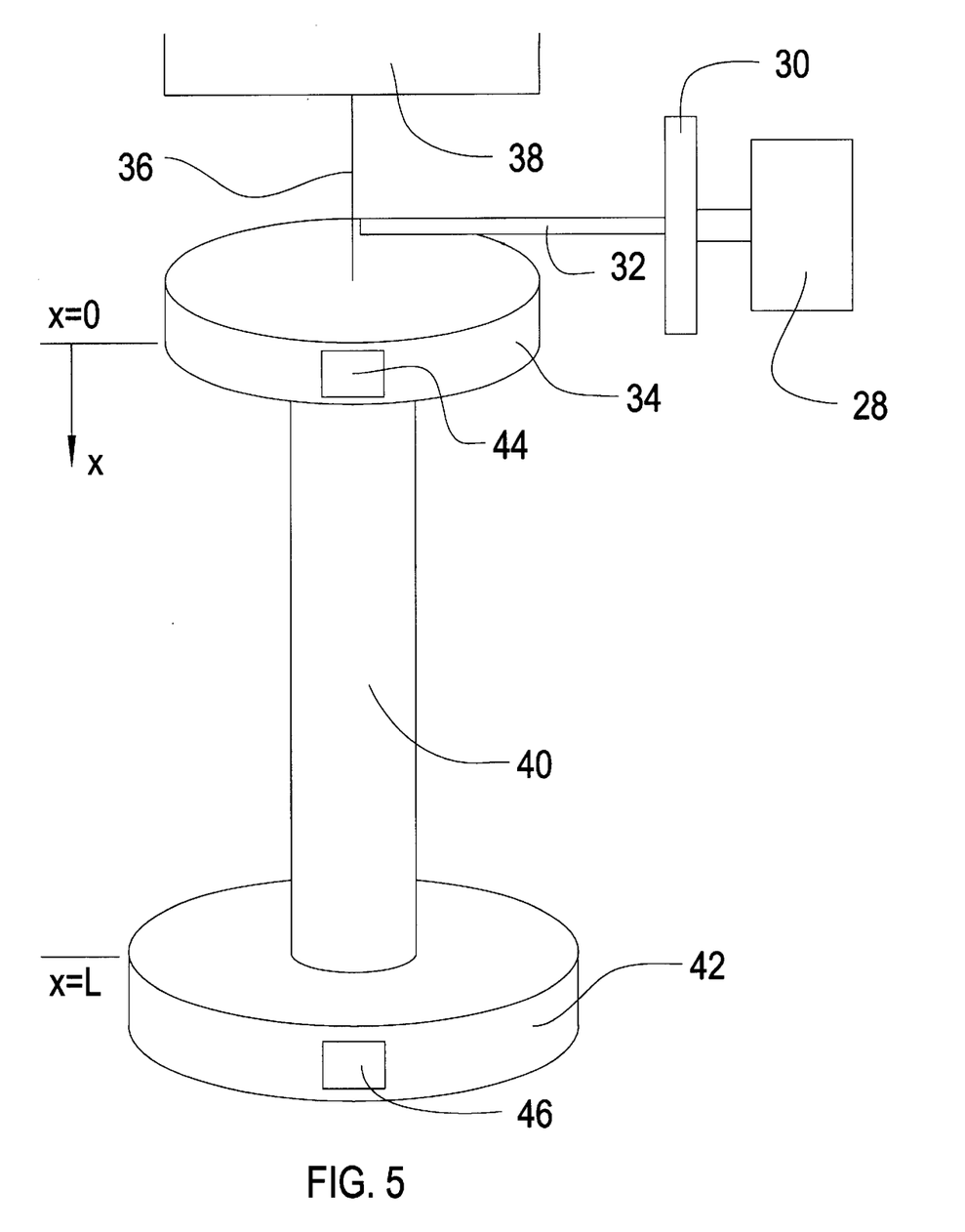
FIG. 5 shows the apparatus required for measurement of the shear modulus of the test specimen.

FIG. 5 shows the apparatus required for measurement of the shear modulus of the test specimen. A shaker 28 having a shaker table 30 is longitudinally connected to a stiff connecting rod 32 that is connected to the edge of a large disc 34. Large disc 34 is mounted using a middle mounted pivot member 36 so that disc 34 is free to rotate about its center point. As shown pivot member 36 suspends disc 34 from a fixed structure 38. A test specimen 40 is rigidly attached to the middle of this disc 34 in a manner so that when disc 34 is pushed by connecting rod 32, it initiates torsional (or rotational) response in test specimen 40. The other end of test specimen 40 is attached to a second disc 42 which acts as rotary inertia when the test is run. Later in this measurement technique, this second disc 42 will be changed to another second disc having a different rotary inertia value so that two sets of experimental measurements can be recorded. Two accelerometers are used. A first accelerometer 44 is attached to the edge of first disc 34, and a second accelerometer 46 is attached to the edge of second disc 42. The measurement axis of both accelerometers 44 and 46 is in the angular direction of the discs 34 and 42. Although both accelerometers measure translation, these values can be converted into angular rotation by multiplying the recorded value by the distance from the center of the disc to the accelerometer for each accelerometer.

In use, shaker 28 inputs energy via shaker table 30 into connecting rod 32 in the form of linear translation. This rod 32 inputs the energy into first disc 34 which makes the disc rotate and initiates a shear wave in the test specimen 40. The speed and loss of this wave can be calculated using measured data from the two accelerometers 44 and 46, and the shear modulus can be calculated from the result. This measurement (estimation) process is extremely similar to the measurement of Young's modulus and is described below.

The system model represents a cylindrical rod attached to a torsional shaker at x=0 and a disc with rotary inertia at x=L. This disc includes an accelerometer to measure the angular acceleration levels at the end of the disc. The linear second order wave equation modeling angular rotation in the specimen 40 is $$\frac{\partial^2 \theta(x,t)}{\partial t^2} - \frac{G}{\rho}\frac{\partial^2 \theta(x,t)}{\partial x^2} = 0, \tag{19}$$

where $\theta(x,t)$ is the angular rotation at location x in meters and time t in seconds, $\rho$ is the density (kg/m$^3$) of the specimen, and G is the frequency dependent, complex shear modulus of elasticity (N/m$^2$) which is unknown and is to be determined using this method. The boundary at x=0 is modeled as a fixed end with harmonic angular motion and is expressed as $$\theta(0,t) = \Theta_0 \exp(\omega t), \tag{20}$$

where $\omega$ is the frequency of excitation (rad/s), $\Theta_0$ is the amplitude (rad), and i is the square root of −1. The boundary at x=L is formulated by matching the angular force (torque) at the end of the specimen 40 to the rotary inertia of the second disc 42 and is expressed as $$GI_p \frac{\partial \theta(L,t)}{\partial x} = -J\frac{\partial^2 \theta(L,t)}{\partial t^2}, \tag{21}$$

where $I_p$ is the polar moment of inertia of the cross-section of the specimen (m$^4$) and J is the rotary inertia of the disc at the end of the bar (kgm$^2$). For a cylindrical rod, the polar moment of inertia is $$I_p = \frac{\pi}{2}a^4. \tag{22}$$

where a is the radius of the specimen in meters (m). For a cylindrical disc, the rotary inertia is $$J = \frac{1}{2}mr^2. \tag{23}$$

where r is the radius of the disc in meters (m), and m is the mass of the disc (kg).

Equation (19) can be rewritten in the spatial domain as $$\frac{d^2 \Theta(x,\omega)}{dx^2} + k_G^2 \Theta(x,\omega) = 0, \tag{24}$$

where $\Theta(x,\omega)$ is the temporal Fourier transform of the axial displacement and $k_G$ is the complex shear wavenumber (rad/m) and is equal to $$k_G = \omega/\sqrt{G/\rho}. \tag{25}$$

Similarly, equation (20) becomes $$\Theta(0,\omega) = \Theta_0, \tag{26}$$

and equation (21) becomes $$GI_p = \frac{d\Theta(L,\omega)}{dx} = J\omega^2 \Theta(L,\omega). \tag{27}$$

The solution to equation (24) is $$\Theta(x,\omega) = X(\omega)\cos(k_G x) + Z(\omega)\sin(k_G x), \tag{28}$$

where X and Z are wave propagation constants. Applying boundary conditions (26) and (27) to equation (28), and writing the solution as a transfer function in the form of a ratio between the rotation at both ends, produces $$\frac{\Theta(L, \omega)}{\Theta_0} = \left[ \frac{1}{\cos(k_G L) - \lambda (k_G L) \sin(k_G L)} \right], \quad (29)$$

where $\lambda$ is equal to $$\lambda = \frac{2J}{a^2 M}, \quad (30)$$

where M is the mass of the specimen expressed as $$M = \rho A L. \quad (31)$$

The transfer function in equation (29) represents data and is a function of unknown wavenumber $k_G$. The inversion of two of these transfer functions using different attached rotary inertial masses will allow the experimental data to be combined and yield a closed form solution of $k_G$ and then G as a function of $\omega$. The theoretical form of these transfer functions is $$\frac{\Theta(L, \omega)}{\Theta_0} = S_1(\omega) = \left[ \frac{1}{\cos(k_G L) - \lambda_1 (k_G L) \sin(k_G L)} \right], \quad (32)$$

and $$\frac{\Theta(L, \omega)}{\Theta_0} = S_2(\omega) = \left[ \frac{1}{\cos(k_G L) - \lambda_2 (k_G L) \sin(k_G L)} \right], \quad (33)$$

where the subscript 1 denotes the first attached rotary inertial mass and the subscript 2 denotes the second attached rotary inertial mass. Writing equations (32) and (33) as a function of $(k_G L)\sin(k_G L)$ and then equating them yields $$\cos(k_G L) = \frac{S_2 \lambda_2 - S_1 \lambda_1}{S_1 S_2 (\lambda_2 - \lambda_1)} = \varphi, \quad (34)$$

where $\varphi$ is a complex quantity. The inversion of equation (34) allows the complex wavenumber to be solved as a function of $\varphi$. This solution to the real part of $k_G$ is $$\text{Re}(k_G) = \begin{cases} \frac{1}{2L} \text{Arccos}(r) + \frac{m\pi}{2L}, & m \text{ even} \\ \frac{1}{2L} \text{Arccos}(-r) + \frac{m\pi}{2L}, & m \text{ odd} \end{cases}, \quad (35)$$

where $$s = [\text{Re}(\varphi)]^2 + [\text{Im}(\varphi)]^2 - \quad (36)$$

$$\sqrt{\{[\text{Re}(\varphi)]^2 + [\text{Im}(\varphi)]^2\}^2 - \{2[\text{Re}(\varphi)]^2 + 2[\text{Im}(\varphi)]^2 - 1\}},$$

m is a non-negative integer and the capital A denotes the principal value of the inverse cosine function. The value of m is determined from the function r, which is a cosine function with respect to frequency. At zero frequency, m is 0. Every time s cycles through $\pi$ radians (180 degrees), m is increased by 1. When the solution to the real part of $k_G$ is found, the solution to the imaginary part of $k_G$ is then written as $$\text{Im}(k_G) = \frac{1}{L} \log_e \left\{ \frac{\text{Re}(\varphi)}{\cos[\text{Re}(k_G) L]} - \frac{\text{Im}(\varphi)}{\sin[\text{Re}(k_G) L]} \right\}. \quad (37)$$

Once the real and imaginary parts of wavenumber $k_G$ are known, the complex valued modulus of elasticity can be determined at each frequency with $$G(\omega) = \text{Re}[G(\omega)] + i\text{Im}[G(\omega)] = \frac{\rho \omega^2}{[\text{Re}(k_G) + i\text{Im}(k_G)]^2}. \quad (38)$$

Equations (19)–(38) produce an estimate shear modulus at every frequency in which a measurement is conducted.

Figure 6:
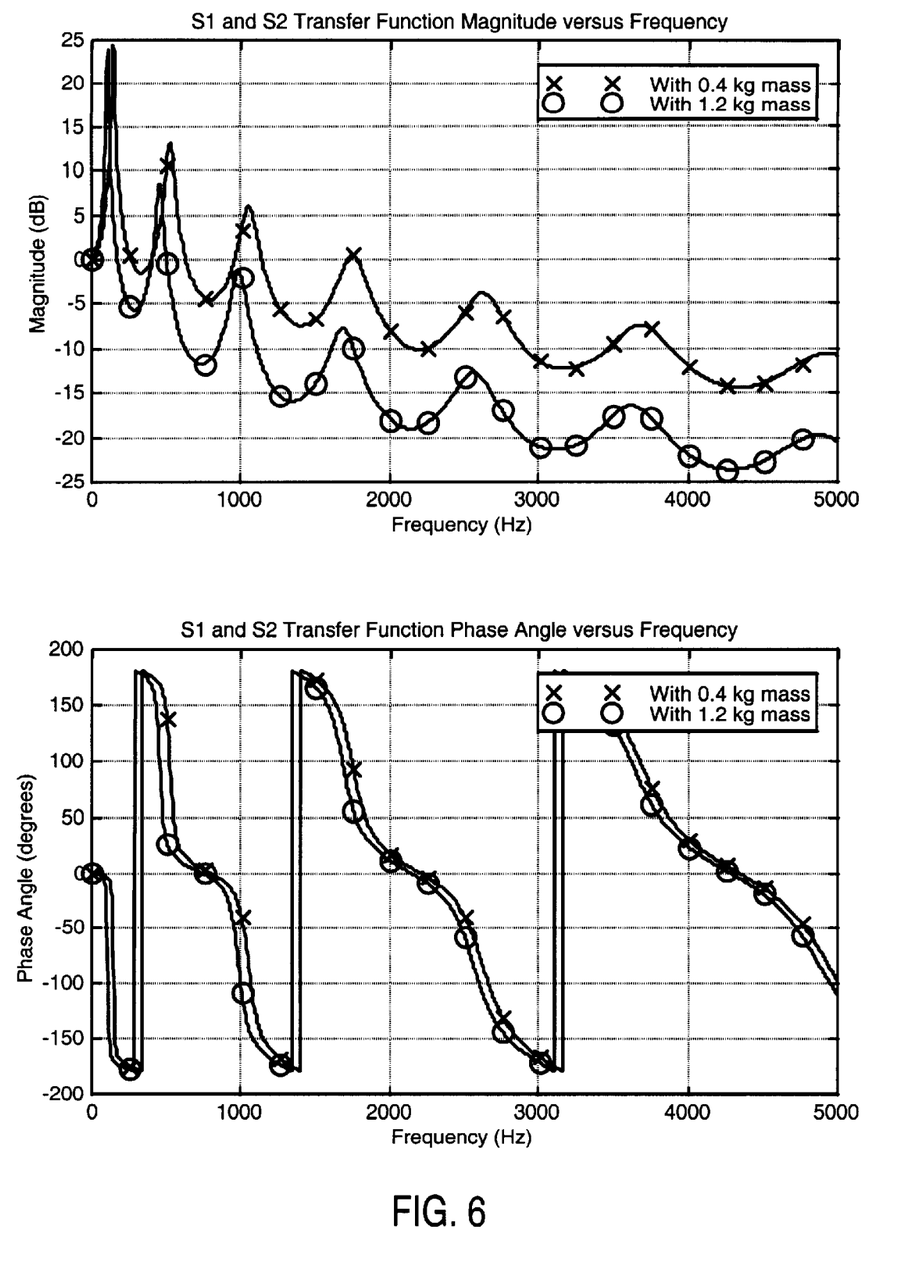
FIG. 6 is a plot of the transfer functions $S_1(\omega)$ and $S_2(\omega)$ versus frequency.
Figure 7:
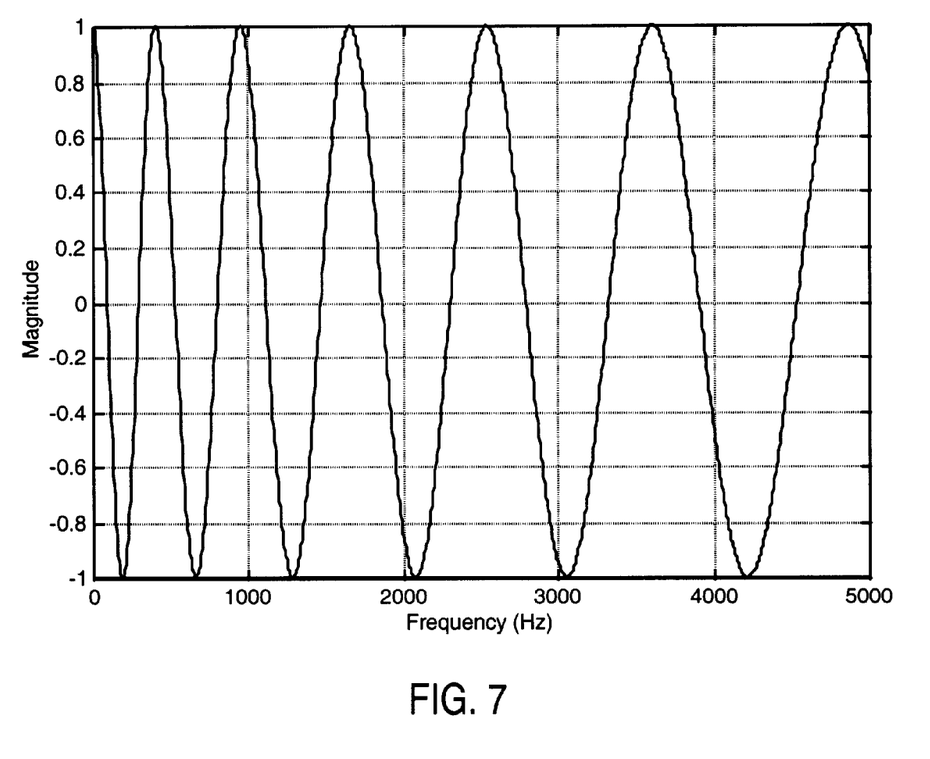
FIG. 7 is a plot of the function r versus frequency.
Figure 8:
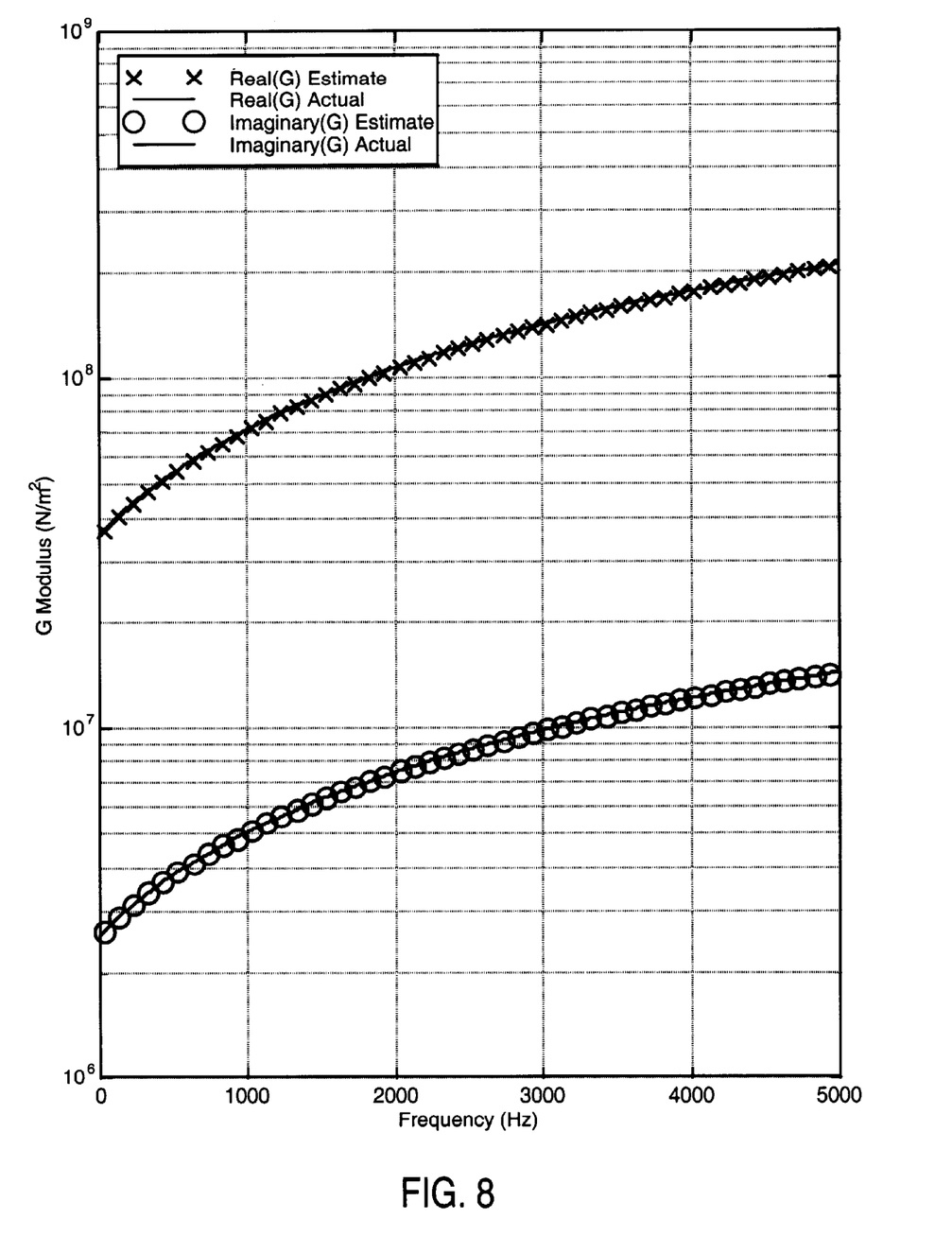
FIG. 8 is a plot of real and imaginary shear modulus values versus frequency.

Numerical simulations are conducted to determine the effectiveness of this method. The baseline problem is also used in this section. One additional parameter needed is the radius of the rotary inertial masses which is chosen to be 0.1016 m. Using the previous mass values the rotary inertia values of the masses are $J_1 = 0.0021$ kgm$^2$ and $J_2 = 0.0062$ kgm$^2$. Using these values, the ratios $\lambda_1$ and $\lambda_2$ are computed to be 0.247 and 0.741, respectively. The shear modulus values used for the analysis are $\text{Re}(G) = 3.58 \times 10^7 + 3.43 \times 10^4$ f N/m$^2$, and $\text{Im}(E) = 2.55 \times 10^6 + 2.34 \times 10^3$ f N/m$^2$ where f is frequency in Hertz. FIG. 6 is a plot of the transfer functions $S_1(\omega)$ and $S_2(\omega)$ versus frequency and corresponds to equations (32) and (33). The top plot is the magnitude and the bottom plot is the phase angle. The first transfer function was computed using an attached mass of 0.4 kg and is depicted with x's and the second transfer function was computed using an attached mass of 1.2 kg and is shown with o's. FIG. 7 is a plot of the function r versus frequency and corresponds to equation (36). Note that although this function is a cosine with respect to frequency, the period is increasing as frequency increases. Values of m versus frequency can be determined from the function r. Once the values of m are known, the modulus values of G can be determined using equations (19)–(38). FIG. 8 is a plot of real and imaginary shear modulus values versus frequency. The real (actual) values used to make the transfer functions are displayed as a solid line and the real (estimated) values are displayed as x's. The imaginary (actual) values used to make the transfer functions are also displayed as a solid line and the imaginary (estimated) values are displayed as o's. The estimated values agree at all frequency values with the actual values. This is expected because there is no noise in the data and all the parameters used to make the transfer functions are used to calculate the modulus values, i.e., no error is introduced when calculating the modulus from the transfer functions.

Figure 9:
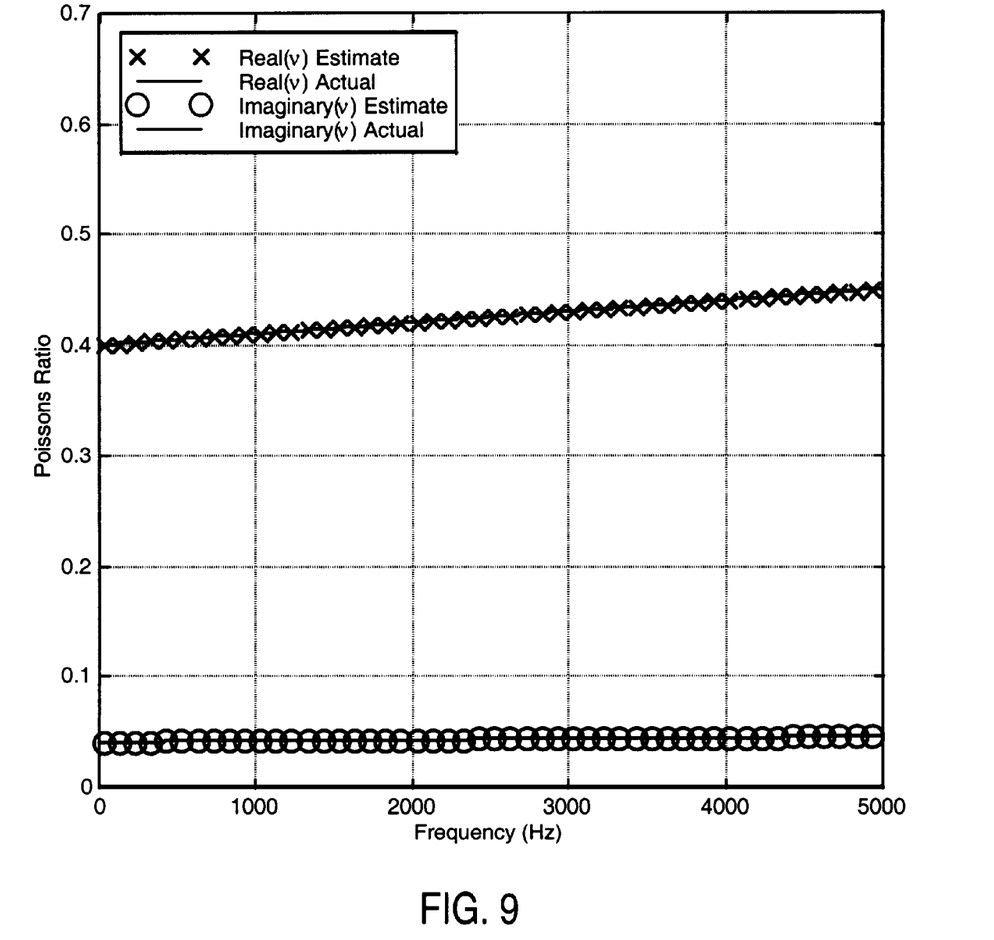
FIG. 9 is a plot of the estimated and actual values of Poisson's ratio versus frequency for a simulation with no noise.

The estimation of Poisson's ratio is achieved by combining Young's modulus and shear modulus that were previously measured. This equation is $$\upsilon = \left[ \frac{E}{2G} \right] - 1, \quad (39)$$

where $\upsilon$ is Poisson's ratio and is dimensionless. The formulation in this method allows for Poisson's ratio to be a complex number, although typically the imaginary part of this number is very small or zero. FIG. 9 is a plot of the estimated and actual values of Poisson's ratio versus frequency for a simulation with no noise. The estimated values of the real part of Poisson's ratio are depicted with x's and the actual values of the real part of Poisson's ratio are shown as a solid line. The estimated values of the imaginary part of Poisson's ratio are depicted with o's and the actual values of the imaginary part of Poisson's ratio are shown as a solid line. The estimated values agree at all frequency values with the actual values. This is expected because there is no noise in the data and all the parameters used to make the transfer functions are used to calculate the moduli values, i.e., no error is introduced when calculating the moduli from the transfer functions.

The major advantage of this new method is that it measures Young's and shear moduli at every frequency that a transfer function measurement is made. It does not depend on system resonances or curve fitting to transfer functions. The calculation from transfer function measurement to calculation of moduli is exact, i.e., no error is introduced during this process. Additionally, numerical simulations show that this method is extremely immune to noise introduced during the transfer function measurement. The new feature introduced in this invention is the method to measure Young's and shear moduli exactly by affixing two different masses having different values to a specimen in linear translation and then again in angular rotation. The transfer function data are collected on a spectrum analyzer and then passed to a computer where the above calculations are performed. Once Young's modulus and shear modulus are determined, Poisson's ratio can be calculated.

Obviously many modifications and variations of the present invention may become apparent in light of the above present teachings. In light of the above, it is therefore understood that within the scope of the appended claims, the invention may be practiced otherwise than as specifically described.

What is claimed is:

1. A method for estimating the real and imaginary Poisson's ratio of a material comprising the steps of:
   providing a first specimen of the material;
   providing an excitation frequency of interest;
   installing said first specimen in a first test apparatus with a first end of said first specimen being joined to a reciprocating motion source and a second end of said first specimen having a mass joined thereto;
   subjecting said first specimen to reciprocating motion at the excitation frequency from said reciprocating motion source;
   recording a first set of accelerations at said first specimen first end;
   recording a second set of accelerations at said first specimen second end;
   calculating the Young's modulus of the material from said obtained first set of accelerations and said obtained second set of accelerations;
   providing a second specimen of the material having a cylindrical configuration;
   installing said second specimen in a second test apparatus with a first end of said second specimen being joined to a reciprocating rotational motion source and a second end of said second specimen having a rotational inertia joined thereto;
   subjecting said second specimen to reciprocating rotational motion at the excitation frequency from said reciprocating motion source;
   recording a third set of accelerations at said second specimen first end;
   recording a fourth set of accelerations at said second specimen second end;
   calculating the shear modulus of the material from said obtained third set of accelerations and said obtained fourth set of accelerations; and
   calculating the Poisson's ratio of the material at the excitation frequency from said calculated Young's modulus and said calculated shear modulus.

2. A method for estimating the real and imaginary Poisson's ratio of a material comprising the steps of:
   providing a first specimen of the material;
   providing an excitation frequency of interest;
   joining the first specimen to a reciprocating motion source;
   providing a first accelerometer on said reciprocating motion source;
   joining a mass at the end of said first specimen away from said reciprocating motion source;
   providing a second accelerometer on said mass;
   providing reciprocating motion at said excitation frequency through an axis of said first specimen;
   obtaining a first set of accelerations at said first accelerometer;
   obtaining a second set of accelerations at said second accelerometer;
   calculating the Young's modulus of said material from said obtained first set of accelerations and said obtained second set of accelerations;
   providing a second specimen of the material having a cylindrical configuration;
   joining the second specimen to a rotational motion source;
   providing a third accelerometer at an edge of said rotational motion source;
   joining a rotational inertia at the end of said second specimen away from said rotational motion source;
   providing a fourth accelerometer on said rotational inertia;
   providing reciprocating rotational motion at said excitation frequency through an axis of said second specimen;
   obtaining a third set of accelerations at said third accelerometer;
   obtaining a fourth set of accelerations at said fourth accelerometer;
   calculating the shear modulus of said material from said obtained third set of accelerations and said obtained fourth set of accelerations; and
   calculating the Poisson's ratio of said material at said excitation frequency from said calculated Young's modulus and said calculated shear modulus.

3. The method of claim 2 wherein:
   said step of calculating the Young's modulus comprises calculating a complex Young's modulus;
   said step of calculating the shear modulus comprises calculating a complex shear modulus; and
   said step of calculating the Poisson's ratio comprises calculating a complex Poisson's ratio from said complex Young's modulus and said complex shear modulus.

4. The method of claim 1 wherein said first specimen and said second specimen are a single specimen of the material having a cylindrical configuration.

5. The method of claim 2 wherein said first specimen and said second specimen are a single specimen of the material having a cylindrical configuration.

* * * * *